(12) United States Patent
Candau et al.

(10) Patent No.: US 6,537,528 B2
(45) Date of Patent: Mar. 25, 2003

(54) COMPOSITION COMPRISING AT LEAST ONE SELF-TANNING AGENT CHOSEN FROM MONOCARBONYL AND POLYCARBONYL COMPOUNDS AND A FLAVYLIUM SALT COMPOUND WHICH IS UNSUBSTITUTED IN POSITION 3, FOR COLORING THE SKIN, AND USES THEREOF

(75) Inventors: Didier Candau, Bievres; Serge Forestier, Claye Souilly, both of (FR)

(73) Assignee: L'Oreal S.A., Paris (FR)

( * ) Notice: Subject to any disclaimer, the term of this patent is extended or adjusted under 35 U.S.C. 154(b) by 71 days.

(21) Appl. No.: 09/901,725

(22) Filed: Jul. 11, 2001

(65) Prior Publication Data

US 2002/0051755 A1 May 2, 2002

(30) Foreign Application Priority Data

Jul. 12, 2000 (FR) ............................................ 00 09118

(51) Int. Cl.$^7$ ............................ A61K 7/42; A61K 7/44; A61K 7/00
(52) U.S. Cl. ............................ 424/59; 424/60; 424/400; 424/401
(58) Field of Search ............................ 424/59, 60, 400, 424/401

(56) References Cited

U.S. PATENT DOCUMENTS

| 4,247,411 A | 1/1981 | Vanlerberghe et al. |
| 4,293,543 A | 10/1981 | Cotte et al. |
| 5,023,327 A | 6/1991 | Yamaoka et al. |

FOREIGN PATENT DOCUMENTS

| CN | 1064284 | 9/1992 |
| CN | 1035512 | 7/1997 |
| EP | 0 903 342 | 3/1999 |
| FR | 2 315 991 | 1/1977 |
| FR | 2 416 008 | 8/1979 |
| FR | 2 466 492 | 4/1981 |
| FR | 2 757 383 | 6/1998 |
| WO | WO 97/35842 | 10/1997 |

OTHER PUBLICATIONS

Co-pending application No. 09/901,724; Attorney Docket No. 05725.0938–00000 Title: Compositions Comprising at Least One UV Screening Agent and at Least One Flavylium Salt Which is Unsubstituted in Position 3, for Coloring the Skin, and Uses Thereof Inventor(s): Didier Candau et al. U.S. Filing Date: Jul. 11, 2001.
Co-pending application No. 09/901,720; Attorney Docket No. 05725.0941–00000 Title: Compositions for Coloring the Skin Comprising at Least One Flavylium Salt Which is Unsubstituted in Position 3 and at Least One Organomodified Silicone Inventor(s): Didier Candau et al. U.S. Filing Date: Jul. 11, 2001.

A. Chardon et al., "Skin Colour Typology and Suntanning Pathways," International Journal of Cosmetic Science, vol. 13, No. 4, pp. 191–208.

David Doig Pratt et al., "A Synthesis of Pyrylium Salts of Anthocyanidin Type. Part II,", Journal of The Chemical Society, vol. CXXIII, 1923, pp. 745–757.

Alexander Robertson et al., "A Synthesis of Pyrylium Salts of Anthocyanidin Type. Part IX. Some Hydroxyflavylium Salts," Journal of The Chemical Society, Jul. 1926, pp. 1951–1959.

Alexander Robertson et al., "A Synthesis of Pyrylium Salts of Anthocyanidin Type. Part XIV," Journal of The Chemical Society, 1927, pp. 2196–2206.

Alexander Robertson et al., "Synthesis of Pyrylium Salts of Anthocyanidin Type. Part XV. The Synthesis of Cyanidin Chloride by Means of O–Benzoylphloroglucinaldehyde," Journal of The Chemical Society, 1928, pp. 1526–1532.

J.G. Sweeny et al., "Synthesis of Anthocyanidins—The Oxidative Generation of Flavylium Cations Using Benzoquinones," Tetrahedron, vol. 33, 1977, pp. 2923–2926.

Janet C. Bell et al., "Experiments on the Synthesis of Anthocyanins. Part XX. Synthesis of Malvidin 3–Galactoside and its Probable Occurrence as a Natural Anthocyanin," Journal of The Chemical Society, 1934, pp. 813–818.

A.D. Bangham et al., "Diffusion of Univalent Ions Across the Lamellae of Swollen Phospholipids," Journal of Molecular Biology, vol. 13, No. 1, Aug. 1965, pp. 238–252.

English language Derwent Abstract of CN 1064284, Sep. 9, 1992.

English language Derwent Abstract of EP 0 903 342, Mar. 24, 1999.

English language Derwent Abstract of FR 2 315 991, Jan. 28, 1977.

English language Derwent Abstract of FR 2 757 383, Jun. 26, 1998.

*Primary Examiner*—Shelley A. Dodson
(74) *Attorney, Agent, or Firm*—Finnegan, Henderson, Farabow, Garrett & Dunner, LLP

(57) ABSTRACT

A cosmetic and/or dermatological composition for giving the skin an artificial coloration, such as a coloration close to that of a natural tan, containing, for example, in a cosmetically acceptable support, at least one self-tanning agent chosen from monocarbonyl compounds and polycarbonyl compounds and at least one flavylium salt compound which is unsubstituted in position 3 and which is substituted with at least one radical chosen from hydroxyl and alkoxy radicals, wherein the at least one flavylium salt compound is, for example, obtained in a manner chosen from synthetically, from a plant extract containing it, and from an enriched plant extract containing it. The invention also relates to the uses of this composition for giving the skin a coloration.

42 Claims, No Drawings

COMPOSITION COMPRISING AT LEAST ONE SELF-TANNING AGENT CHOSEN FROM MONOCARBONYL AND POLYCARBONYL COMPOUNDS AND A FLAVYLIUM SALT COMPOUND WHICH IS UNSUBSTITUTED IN POSITION 3, FOR COLORING THE SKIN, AND USES THEREOF

The present invention relates to cosmetic and/or dermatological compositions for artificially coloring the skin, comprising, for example, in a cosmetically acceptable support; at least one self-tanning agent chosen from monocarbonyl compounds and polycarbonyl compounds and at least one flavylium salt compound which is unsubstituted in position 3, which is substituted with at least one radical chosen from hydroxyl and alkoxy radicals, wherein the at least one flavylium salt compound may be obtained, for example, in a manner chosen from synthetically, from a plant extract containing it, and from an enriched plant extract containing it.

The invention also relates to the use of the composition for coloring the skin.

Nowadays, it is important to look healthy, and a tanned skin is always a sign of good health. However, a natural tan may not always be desirable since it requires long exposure to UV radiation, for example to UV-A radiation which causes the tanning of the skin. UV-A radiation is also liable to induce an adverse change of the skin, for example in the case of sensitive skin or skin which is continually exposed to solar radiation. It may thus be desirable to find an alternative to a natural tan which may be compatible with the requirements of such skin types.

Most of the cosmetic products intended for artificially tanning the skin are based on monocarbonyl and polycarbonyl compounds which, by interacting with the amino acids in the skin, allow the formation of colored products.

To this end, it is known that dihydroxyacetone, or DHA, is a product which is commonly used in cosmetics as an agent for artificially tanning the skin. When applied to the skin, for example to the face, it gives a tanning or bronzing effect which may be similar in appearance to that which may result from prolonged exposure to sunlight (a natural tan) or under a UV lamp.

One drawback of DHA can be the length of time the coloration takes to develop. Specifically, several hours (3 to 5 hours in general) may be required for the coloration to be revealed. Furthermore, the coloration produced on the skin by DHA may often be considered as too yellow by users.

Thus, efforts are still under way to find novel compounds and novel compositions which can give the skin an artificial coloration, for example, close to that of a natural tan, in at least one of a simple, effective, fast, and risk-free manner.

Anthocyanin colorants have been known for a long time as pharmaceutical and food colorants. These anthocyans may be present in nature in the form of heterosides known as anthocyanosides and genins, known as anthocyanidines. These anthocyans may be phenyl-2-benzopyrylium derivatives and flavylium derivatives and may be present, for example, in the plant in the form of salts. Anthocyans may be red-, violet- or blue-colored compounds which generally color flowers, fruit, and occasionally leaves. The color observed may depend both on the structure of the predominant genin and on the conditions of the medium in which the anthocyanin colorants are present.

Now, after considerable research conducted in the field of artificial coloring of the skin, the Inventors have discovered that the combination of at least one self tanning agent chosen from monocarbonyl compounds and polycarbonyl compounds, for example DHA, and at least one flavylium salt compound unsubstituted in position 3, may give the skin, after the product has been applied thereto, an artificial coloration, for example, a coloration close to that of a natural tan. Specifically, the Inventors have found that the combination may make it possible to obtain, compared with a self-tanning agent of the carbonyl type for example DHA used alone, an increase in color on the skin in a much shorter time (for example after 30 minutes). Furthermore, the combination may make it possible to obtain a shade which may be close to that of a natural tan and which may be stable over time.

One subject of the present invention is thus a novel cosmetic and/or dermatological composition for giving the skin an artificial coloration, for example, close to that of a natural tan, comprising, for example, in a cosmetically acceptable support, at least one self-tanning agent chosen from monocarbonyl compounds and polycarbonyl compounds, and at least one flavylium salt compound which is unsubstituted in position 3 and which is substituted with at least one radical chosen from hydroxyl and alkoxy radicals, wherein the at least one flavylium salt compound may be, for example, obtained in a manner chosen from synthetically, from a plant extract containing it, and from an enriched plant extract containing it.

A subject of the present invention is also the novel use of the combination of at least one self-tanning agent chosen from a monocarbonyl compound and a polycarbonyl compound, and at least one flavylium salt compound which is unsubstituted in position 3 and which is substituted with at least one radical chosen from hydroxyl and alkoxy radicals, for example, obtained in a manner chosen from synthetically, from a plant extract containing it, and from an enriched plant extract containing it, in cosmetic and/or dermatological compositions, with the aim of giving the skin an artificial coloration, for example, close to that of a natural tan.

A subject of the present invention is also a process for giving the skin an artificial coloration, for example, close to that of a natural tan, comprising applying to the skin an effective amount of a combination of at least one self-tanning agent chosen from monocarbonyl compounds and polycarbonyl compounds, and at least one flavylium salt compound which is unsubstituted in position 3 and which is substituted with at least one radical chosen from hydroxyl and alkoxy radicals, obtained, for example, in a manner chosen from synthetically, from a plant extract, and from an enriched plant extract, in a cosmetic composition.

The composition and uses in accordance with the invention may make it possible to obtain an artificial coloration, for example, close to that of a natural tan, in a very short space of time. Thus, an immediate coloration may be obtained, which may allow at least one of the following properties: visualization of the application, and better homogeneity in the spreading of the composition on the skin and thus of the resulting coloration. Furthermore, the artificial coloration obtained on the skin according to the invention may be extremely close to that of a natural tan.

For the purposes of the present invention, the expression "composition intended for artificially coloring the skin" will be understood to mean a formulation with a particular affinity for the skin which allows it to give the skin a long-lasting coloration. The formulation may be at least one of non-covering (does not have a tendency to opacify the skin), not removed either with water or with a solvent, and able to withstand both rubbing and washing with a solution containing surfactants. Such a long-lasting coloration may thus be distinguished from the superficial and transient coloration provided, for example, by a make-up product.

Other characteristics, aspects and advantages of the present invention, at least one of which may be present in a specific embodiment, will become apparent on reading the detailed description which follows.

For example, the composition, in accordance with the present invention, may, for example, generally lead, 30 minutes after application to a fair skin at a rate of 2 mg/cm$^2$, to a darkening characterized in the (L*, a*, b*) calorimetric measuring system by a $\Delta L^*$ ranging from −0.5 to −20. For example, $\Delta L^*$ may range from −0.5 to −15.

For example, the composition, in accordance with the present invention, may give, 30 minutes after application to the skin at a rate of 2 mg/cm$^2$, a coloration on a fair skin which may be defined in the (L*, a*, b*) colorimetric measuring system, by a ratio $\Delta a^*/\Delta b^*$ ranging from 0.5:1:3:1, and for example ranging from 0.8:1:2:1.

According to the present invention, the term "fair skin" should be understood to indicate an untanned skin whose calorimetric characteristics may be defined by its ITA angle as defined in the publication by A. Chardon et al. "Skin Color Typology and Suntanning Pathways" presented at the 16th IFSCC congress, Oct. 8-10, 1990, New York, and in Int. J. Cosm. Sci. 13 191-208 (1991), the disclosures of both references relating to such calorimetric characteristics are hereby incorporated by reference. The fair skin as defined in this classification may have an ITA angle ranging from 35 to 55.

In the (L*, a*, b*) calorimetric measuring system: L* is luminance or clarity, a* is the red-green axis (−a*=green, +a*=red) and b* is the yellow-blue axis (−b*=blue, +b*=yellow). Thus, a* and b* express the shade of the skin.

$\Delta L^*$ reflects the darkening of the color: the more negative the $\Delta L^*$, the darker the color becomes, with: $\Delta L^*=L^*$ uncolored skin–L* colored skin The ratio $\Delta a^*/\Delta b^*$ reflects the red/yellow balance and thus the shade, with:
$\Delta a^*=a^*$ uncolored skin–a* colored skin
$\Delta b^*=b^*$ uncolored skin–b* colored skin The at least one flavylium salt compound which may be unsubstituted in position 3, in accordance with the invention, which may, for example, be used are those corresponding to formula (I) below:

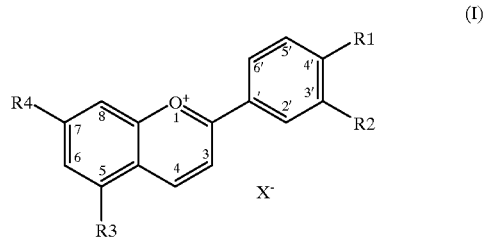

wherein:
R1 is chosen from an OH radical and linear and branched, saturated and unsaturated (C$_1$-C$_8$) alkoxy radicals,
R$_2$, R$_3$ and R$_4$, which may be identical or different, are chosen from H and R$_1$,
it being understood that, for example, in one embodiment of the invention, at least one of the radicals R$_1$ to R$_4$ is OH,
X— is chosen from organic anions, mineral anions, and for example, from mineral acid derivatives chosen from, for example, halides, for example bromide and chloride; and organic acid derivatives chosen from, for example, acetate, borate, citrate, tartrate, lactate, bisulphate, sulphate, and phosphate.

The at least one flavylium salt compound of formula (I) may be, according to the present invention, chosen from a group for which, in formula (I), R$_1$ is chosen from OH and OCH$_3$.

Among these, mention may be made, for example, of the chlorides of the following compounds:
4',5,7-trihydroxyflavylium, commonly known as "apigeninidine chloride",
3',4',7-trihydroxyflavylium,
4'-hydroxyflavylium,
4',7-dihydroxyflavylium,
3',4'-dihydroxyflavylium,
3',4'-dihydroxy-7-methoxyflavylium,
3',4',5,7-tetrahydroxyflavylium, and
3',4',5',5,7-pentahydroxyflavylium.

For example, the at least one flavylium salt compound may be chosen from at least one of apigeninidine chloride (4',5,7-trihydroxyflavylium chloride) and 3',4',7-trihydroxyflavylium chloride. These compounds can be prepared in pure form, i.e., in a form at least 90% pure.

According to certain embodiments, the present invention comprises using apigeninidine chloride in the form of, or derived from, a plant extract, which can be readily prepared by extraction and isolation from leaves of *Sorghum caudatum* according to, for example, at least one of the processes disclosed in patents CN 1,064,284A and CN 1,035,512C, the disclosures in both patents directed to said extraction and/or isolation are hereby incorporated by reference, and variants of these processes.

According to certain embodiments, the at least one flavylium salt compound may be chosen from those extracted from at least one of the stems, seeds, and leaves of *Sorghum bicolour*; the petals of *Gesneria fulgens*; and at least one of the species *Blechum procerum* and Sorghum in combination with *Colletotrichum graminicola*.

According to certain embodiments, the present invention comprises using an extract from the leaves of *Sorghum bicolour*, which can be obtained by an aqueous-alcoholic extraction in acidic medium at an extraction temperature ranging from 30 to 40° C. with a ratio of the volume of solvent to the mass of *Sorghum bicolor* leaves ranging from 10:1 to 30:1. The Sorghum plant extract can have an approximate titre ranging from 0.05% to 50% by weight of apigeninidine chloride.

The at least one flavylium salt compound which is unsubstituted in position 3 and which is substituted with at least one radical chosen from a hydroxyl radical and an alkoxy radical, may be readily and/or cheaply obtained by synthesis, for example, by the well-known method of R. Robinson and D. Pratt, J. Chem. Soc. 745 (1923), the disclosure of which directed to said synthesis is hereby incorporated by reference. The method comprises condensing at least one of an ortho-hydroxybenzaldehyde and a substituted ortho-hydroxybenzaldehyde with at least one of an acetophenone and a substituted acetophenone to yield, by selecting the substituents, a desired at least one flavylium salt compound, corresponding to formula (I).

Taking apigeninidine chloride (4',5,7-trihydroxyflavylium chloride) as an example, the synthetic scheme (i) may be as follows:

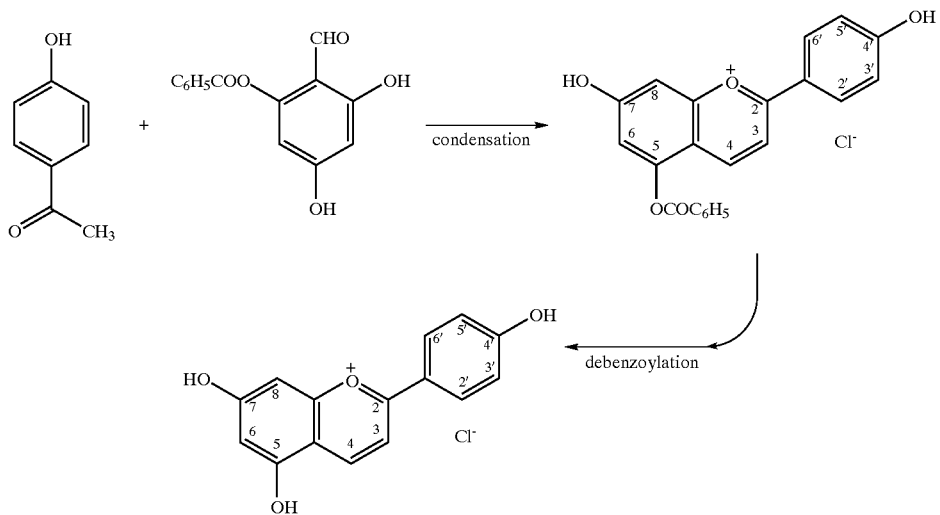

Taking 3',4',7-trihydroxyflavylium chloride as an example, the synthetic scheme (ii) may be as follows:

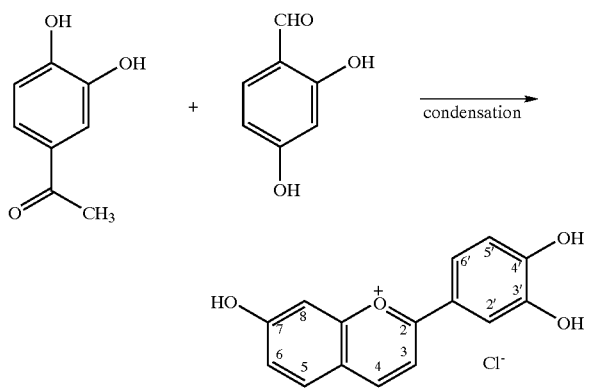

A variety of synthetic routes, for example those that are well known in the field, may be used to lead to apigeninidine.

One method for preparing apigeninidine comprises, for example, in a first step, preparing trimethylapigeninidine by condensing commercial 4,6-dimethoxy-2-hydroxybenzaldehyde with commercial 4-methoxyacetophenone in an anhydrous ether medium at 0° C., and saturating with anhydrous HCl, to yield, after filtration, an orange-red precipitate of trimethylapigeninidine. In a second step, the trimethylapigeninidine obtained in the preceding step is hydrolyzed to apigeninidine chloride, the reaction being carried out in a medium of HI and phenol and AgCl dissolved in methanol. Such a synthetic method is disclosed for example, by R. Robinson and A. Robertson in J. Chem. Soc. 1951 (1926) and 2196 (1927), the disclosure of which directed to said synthesis is incorporated herein by reference.

Another method, for example, for preparing apigeninidine comprises condensing 2,4,6-trihydroxybenzaldehyde with 4-hydroxyacetophenone at 0° C. in an anhydrous solvent medium, for example ethyl acetate, and saturating with anhydrous HCl, to yield apigeninidine chloride. Such a method is disclosed, for example, by R. Robinson and A. Robertson in J. Chem. Soc. 1528 (1928), the disclosure of which directed to said synthesis is hereby incorporated by reference.

Another method, for example, for preparing apigeninidine chloride comprises reducing at least one of a flavone, naringenin, and triacetyl derivatives thereof, with $NaBH_4$, and then oxidizing the product obtained with chloranil (tetrachloro-1,4-benzoquinone). The method is disclosed, for example, by J. G. Sweeny and G. A. Iacobucci in the review Tetrahedron 33 2923-2927 (1977), the disclosure of which directed to said synthesis is hereby incorporated by reference.

As a further example, use may be made of a method comprising condensing 2,4-dihydroxy-6-benzoyloxybenzaldehyde with 4-hydroxyacetophenone at 0° C. in an anhydrous ethyl acetate medium, saturating with anhydrous HCl and then debenzoylating the product obtained with sodium hydroxide, to yield apigeninidine chloride in high yield, according to scheme (i) described above. The method is disclosed, for example, by R. Robinson and J. C. Bell in J. Chem. Soc. 813 (1934), the disclosure of which directed to said synthesis is hereby incorporated by reference.

The concentration of the at least one flavylium salt compound as described according to the present invention may range, for example, from about 0.0001% to 10%, for further example, from 0.001% to 5%, by weight relative to the total weight of the composition.

The monocarbonyl and polycarbonyl compounds may be chosen, for example, from isatin, alloxane, ninhydrin, glyceraldehyde, mesotartaric aldehyde, glutaraldehyde, erythrulose, pyrazoline-4,5-dione derivatives as disclosed in patent application FR 2 466 492 and WO 97/35842, the disclosures of both of which related to such compounds are hereby incorporated by reference, dihydroxyacetone (DHA), 4,4-dihydroxypyrazolin-5-one derivatives as disclosed in patent application EP 903 342, the disclosure of which related to such compounds is hereby incorporated by reference. These self-tanning agents may be combined with direct dyes and indole derivatives.

In another embodiment of the invention, use will be made, for example, of dihydroxyacetone (DHA).

The monocarbonyl and polycarbonyl compounds are generally present in the composition according to the invention in an amount ranging, for example, from 0.1% to 10% by weight relative to the total weight of the composition, and for further example ranging from 0.2% to 8% by weight relative to the total weight of the composition.

The composition in accordance with the present invention may also comprise at least one conventional cosmetic adjuvant chosen, for example, from fatty substances, organic solvents, ionic thickeners, nonionic thickeners, softeners, antioxidants, free-radical scavengers, opacifiers, stabilizers, emollients, silicones, a-hydroxy acids, antifoams, moisturizers, vitamins, fragrances, preserving agents, surfactants, fillers, polymers, propellants, acidifying agents, basifying agents, colorants, and any other ingredient usually used in cosmetics and/or dermatology, for example, for manufacturing antisun compositions in the form of emulsions.

The fatty substances may be chosen from oils, waxes. The term "oil" should be understood to indicate a compound which is liquid at room temperature. The term "wax" should be understood to indicate a compound which is solid or substantially solid at room temperature and whose melting point is generally greater than 35° C.

Oils which may be mentioned include mineral oils (paraffin); plant oils (sweet almond oil, macadamia oil, blackcurrent seed oil, jojoba oil); synthetic oils, for example perhydrosqualene, fatty alcohols, fatty acids, and fatty esters (for example the ($C_{12}$-$C_{15}$) alkyl benzoate sold under the trade name FINSOLV TN by the company Finetex, octyl palmitate, isopropyl lanolate, triglycerides including those of capric/caprylic acid), oxyethylenated fatty esters, oxypropylenated fatty esters, and ethers; silicone oils (cyclomethicone, polydimethylsiloxanes or PDMSs) and fluoro oils, and polyalkylenes.

Waxy compounds which may be mentioned include paraffin, carnauba wax, beeswax, and hydrogenated castor oil.

Among the organic solvents which may be mentioned are lower alcohols and polyols.

According to one embodiment, the composition according to the invention may comprise at least 5% by weight, relative to the weight of the composition, of at least one polyhydroxylated solvent. The solvent may be chosen from glycols and glycol ethers, for example ethylene glycol, propylene glycol, butylene glycol, dipropylene glycol and diethylene glycol. For example, the composition according to the invention can comprisea mixture of at least three different polyhydroxylated solvents and as a further example a mixture comprising propylene glycol, butylene glycol and dipropylene glycol.

The thickeners may be chosen, for example, from crosslinked polyacrylic acids, modified guar gums, unmodified guar gums and celluloses, chosen from hydroxyprolyl guar gum, methylhydroxyethylcellulose and hydroxypropylmethylcellulose.

Needless to say, a person skilled in the art will take care to select the optional additional compound(s) mentioned above and/or the amounts thereof such that at least one advantageous property intrinsically associated with the combination in accordance with the invention is not, or is not substantially, adversely affected by the addition(s) envisaged.

The composition according to the invention may be prepared according to techniques that are well known to those skilled in the art, for example those intended for preparing oil-in-water and water-in-oil emulsions.

This composition may be, for example, in at least one form chosen from simple emulsions, complex (O/W, W/O, O/W/O and W/O/W) emulsions (such as creams and milks), gels, cream-gels, lotions, powders, solid tubes, aerosols, mousses, and sprays.

The composition according to the invention may, for example, be in a form chosen from an oil-in-water emulsion and a water-in-oil emulsion.

When it is an emulsion, the aqueous phase of this emulsion may comprise a nonionic vesicular dispersion prepared according to known processes (Bangham, Standish and Watkins, J. Mol. Biol. 13, 238 (1965), FR 2 315 991 and FR 2 416 008), the disclosures of all of which related to such vesicular dispersions are hereby incorporated by reference.

Unless otherwise indicated, all numbers expressing quantities of ingredients, properties such as molecular weight, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. The examples which follow are intended to illustrate the invention without, however, limiting its scope.

EXAMPLE 1

An extract of *Sorghum bicolor* with a titre of 20-30% of apigeninidine chloride was prepared according to the following preparation process:

An extract from the leaves of *Sorghum bicolor* was obtained by aqueous-alcoholic (95° ethanol) extraction in acidic medium (0.2% HCl) at an extraction temperature of 35° C. with a ratio of the volume of solvent to the mass of *Sorghum bicolor* leaves of 15:1. The Sorghum plant extract was oven-dried for 24 h at 40° C. and screened at 200 µm.

The yield for this extraction was 22.42% colorant matter.

The titre for the extract thus obtained was 21% by weight of apigeninidine chloride.

This example was intended to show the intensity of the coloration obtained with an extract of *Sorghum bicolor* combined with DHA in accordance with the present invention, and also the speed with which this coloration developed compared with a composition containing DHA as skin-coloring agent.

This example was intended to show that the coloration obtained by the combination of DHA with an extract of *Sorghum bicolor* in accordance with the present invention gave a color intensity which was strong immediately after application and which was stable over time.

The Inventors prepared the following compositions (the amounts are expressed as percentages by weight relative to the total weight of the composition):

| Composition A (not according to the invention): | |
|---|---|
| Polydimethyl/methyl siloxane POE/POP (396/4) (EO/PO 18/18) at 10% D5 | 10 g |
| Cyclopentadimethylsiloxane | 12.5 g |
| Mixture of natural tocopherols/soybean oil | 0.1 g |
| Dihydroxyacetone (DHA) | 4 g |
| Sodium chloride | 2 g |
| Propylene glycol | 23 g |
| Butylene glycol | 5 g |
| Dipropylene glycol | 10 g |
| Trisodium citrate | 0.542 g |
| Citric acid | 0.209 g |
| Demineralized water | 32.649 g |

| Composition B (invention): | |
|---|---|
| Polydimethyl/methyl siloxane POE/POP (396/4) (EO/PO 18/18) at 10% D5 | 10 g |
| Cyclopentadimethylsiloxane | 12.5 g |
| Mixture of natural tocopherols/soybean oil | 0.1 g |
| Demineralized water | 32.55 g |
| Sodium chloride | 2 g |
| Propylene glycol | 23 g |
| Butylene glycol | 5 g |
| Dipropylene glycol | 10 g |
| Extract of Sorghum bicolor as prepared above | 0.1 g |
| Dihydroxyacetone | 4 g |
| Trisodium citrate | 0.542 g |
| Citric acid | 0.208 g |

Evaluation Protocol

Compositions A and B were applied at a rate of 2 mg/cm$^2$ to an area of 7×4.5 cm$^2$ delimited on the back of six volunteers whose skin color, characterized by the ITA angle, was from 35 to 55.

The five series of calorimetric measurements below were carried out using a Minolta CR-300 calorimeter:
1) before applying the composition,
2) 30 minutes after the application,
3) 2 hours after application,
4) 4 hours after application, The results were expressed in the (L$^*$, a$^*$, b$^*$) system in which L$^*$ is the luminance, a$^*$ is the red-green axis (−a$^*$ = green, +a$^*$ =red) and b$^*$ is the yellow-blue axis (−b$^*$ =blue, +b$^*$ =yellow). Thus, a$^*$ and b$^*$ expressed the shade of the skin.

To evaluate the intensity of the coloration, the important value was the ΔL$^*$ which reflected the darkening of the color: the more negative the ΔL$^*$, the more the color is darkened, with:
ΔL$^*$=L$^*$ uncolored skin−L$^*$ colored skin For the shade of the coloration obtained, the important value was the ratio Δa$^*$/Δb$^*$ which reflected the red/yellow balance and thus the shade, with:
Δa$^*$=a$^*$ uncolored skin−a$^*$ colored skin
Δb$^*$=b$^*$ uncolored skin−b$^*$ colored skin The results obtained were collated in Table (I) below:

TABLE (I)

| | Composition A (comparative) ΔL$^*$ | Composition B (invention) ΔL$^*$ | Composition B (invention) Δa$^*$/Δb$^*$ |
|---|---|---|---|
| 30 minutes | −0.4 | −1.6 | 0.8 |
| 2 hours | −1.1 | −2.0 | 0.7 |
| 4 hours | −2.5 | −2.7 | 0.9 |

It was thus found that 30 minutes after the application, composition B containing DHA and the coloring plant extract gave a darkening of the skin which was close to that obtained with composition A containing only DHA, after 4 hours.

Composition B containing DHA and the coloring plant extract also gave a shade which was close to that of a natural tan and which was basically constant over time.

What is claimed is:

1. A cosmetic and/or dermatological composition for giving the skin an artificial coloration comprising,
   at least one self-tanning agent chosen from monocarbonyl compounds and polycarbonyl compounds, and
   at least one flavylium salt compound which is unsubstituted in position 3 and which is substituted with at least one radical chosen from hydroxyl and alkoxy radicals.

2. The composition according to claim 1, wherein the artificial coloration is close to that of a natural tan.

3. The composition according to claim 1, further comprising a cosmetically acceptable support.

4. The composition according to claim 1, wherein the composition produces, 30 minutes after application to a fair skin at a rate of 2 mg/cm$^2$, a darkening of color of the skin wherein ΔL$^*$ ranges from −0.5 to −20.

5. The composition according to claim 4, wherein the ΔL$^*$ ranges from −0.5 to −15.

6. The composition according to claim 1, wherein the composition produces, 30 minutes after application to a fair skin at a rate of 2 mg/cm2, a coloration defined by a ratio Δa$^*$/Δb$^*$ ranging from 0.5:1 to 3:1.

7. The composition according to claim 6, wherein the ratio Δa$^*$/Δb$^*$ ranges from 0.8:1 to 2:1.

8. The composition according to claim 1, wherein the at least one flavylium salt compound corresponds to formula (I) below:

$$\text{(I)}$$

wherein:
R$_1$ is chosen from an OH radical and linear and branched, saturated and unsaturated (C$_1$-C$_8$) alkoxy radicals,
R$_2$, R$_3$ and R$_4$, which may be identical or different, are chosen from H and R$_1$, it being understood that at least one of the radicals R$_1$ to R$_4$ is OH,
X$^-$ is chosen from organic anions and mineral anions.

9. The composition according to claim 8, wherein X$^-$ is chosen from halides and organic acid derivatives.

10. The composition according to claim 8, wherein R$_1$ is chosen from OH and OCH$_3$.

11. The composition according to claim 8, wherein the at least one flavylium salt compound corresponding to formula (I) is chosen from the chloride of the following compounds:
4',5,7-trihydroxyflavylium,
3',4',7-trihydroxyflavylium,
4'-hydroxyflavylium,
4',7-dihydroxyflavylium,
3',4'-dihydroxyflavylium,
3',4'-dihydroxy-7-methoxyflavylium,
3',4',5,7-tetrahydroxyflavylium, and
3',4',5',5,7-pentahydroxyflavylium.

12. The composition according to claim 11, wherein the at least one flavylium salt compound is chosen from 4',5,7-trihydroxyflavylium chloride.

13. The composition according to claim 12, wherein the 4',5,7-trihydroxyflavylium chloride is in pure form, which can be obtained synthetically.

14. The composition according to claim 12, wherein the 4',5,7-trihydroxyflavylium chloride is in the form of a plant extract.

15. The composition according to claim 14, wherein the plant extract is chosen from extractions from leaves of

*Sorghum caudatum;* from at least one of stems, seeds and leaves of *Sorghum bicolor,* from the petals of *Gesneria fulgens,* and from at least one of the species *Blechum procerum* and Sorghum in combination with *Colletotrichum graminicola.*

16. The composition according to claim 14, wherein the plant extract is an extract of *Sorghum bicolor* obtained by an acidic aqueous-alcoholic extraction at an extraction temperature ranging from 30° C. to 40° C. with a ratio of the volume of solvent to the mass of *Sorghum bicolor* leaves ranging from 10:1 to 30:1.

17. The composition according to claim 16, wherein the extract of *Sorghum bicolor* has a titre ranging from 0.05% to 50% by weight of 4',5,7-trihydroxyflavylium salt.

18. The composition according to claim 1, wherein a concentration of the at least one flavylium salt compound ranges from 0.0001% to 10% by weight relative to the total weight of the composition.

19. The composition according to claim 18, wherein a concentration of the at least one flavylium salt compound ranges from 0.001% to 5% by weight relative to the total weight of the composition.

20. The composition according to claim 1, wherein the at least one self-tanning agent is chosen from isatin, alloxane, ninhydrin, glyceraldehyde, mesotartaric aldehyde, glutaraldehyde, erythrulose, pyrazoline-4,5-dione derivatives, dihydroxyacetone, and 4,4-dihydroxypyrazolin-5-one derivatives.

21. The composition according to claim 1, wherein the at least one self-tanning agent is is combined with one of direct dyes and indole derivatives.

22. The composition according to claim 1, wherein the at least one self-tanning agent is dihydroxyacetone.

23. The composition according to claim 1, wherein the at least one self-tanning agent is present in the composition in an amount ranging from 0.1% to 10% by weight relative to the total weight of the composition.

24. The composition according to claim 1, further comprising at least 5% by weight, relative to the weight of the composition, of at least one polyhydroxylated solvent.

25. The composition according to claim 24, wherein the at least one polyhydroxylated solvent is chosen from glycols and glycol ethers.

26. The composition according to claim 24, wherein the at least one polyhydroxylated solvent is chosen from ethylene glycol, propylene glycol, butylene glycol, dipropylene glycol, and diethylene glycol.

27. The composition according to claim 1, further comprising a mixture of three different polyhydroxylated solvents.

28. The composition according to claim 1, further comprising a mixture comprising propylene glycol, butylene glycol, and dipropylene glycol.

29. A cosmetic and/or dermatological composition intended for giving the skin an artificial coloration comprising,
at least one self-tanning agent chosen from monocarbonyl compounds and polycarbonyl compounds, and
at least one flavylium salt compound which is unsubstituted in position 3 and which is substituted with at least one radical chosen from hydroxyl and alkoxy radicals.

30. The composition according to claim 29, wherein the artificial coloration is close to that of a natural tan.

31. A cosmetic and/or dermatological composition intended for giving the skin an artificial coloration comprising,
at least one self-tanning agent chosen from monocarbonyl compounds and polycarbonyl compounds, and
at least one flavylium salt compound which is unsubstituted in position 3, which is substituted with at least one radical chosen from hydroxyl and alkoxy radicals, and which is obtained in a manner chosen from synthetically, from a plant extract containing it, and from an enriched plant extract containing it.

32. A cosmetic and/or dermatological composition for giving the skin an artificial coloration comprising,
at least one self-tanning agent chosen from monocarbonyl compounds and polycarbonyl compounds, and
at least one flavylium salt compound which is unsubstituted in position 3, which is substituted with at least one radical chosen from hydroxyl and alkoxy radicals, and which is obtained in a manner chosen from synthetically, from a plant extract containing it, and from an enriched plant extract containing it.

33. A cosmetic treatment process for giving to skin an artificial coloration comprising,
applying to the skin an effective amount of a composition comprising,
at least one self-tanning agent chosen from monocarbonyl compounds and polycarbonyl compounds, and
at least one flavylium salt compound which is unsubstituted in position 3 and which is substituted with at least one radical chosen from hydroxyl and alkoxy radicals.

34. The process according to claim 33, wherein the artificial coloration is close to that of a natural tan.

35. The process according to claim 33, wherein the at least one flavylium salt compound corresponds to formula (I) below:

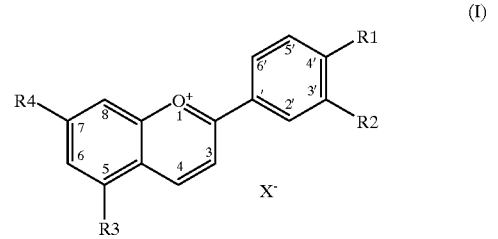

(I)

wherein:

$R_1$ is chosen from an OH radical and linear and branched, saturated and unsaturated ($C_1$-$C_8$) alkoxy radicals, $R_2$, $R_3$ and $R_4$, which may be identical or different, are chosen from H and $R_1$, it being understood that at least one of the radicals $R_1$ to $R_4$ is OH, $X^-$ is chosen from organic anions and mineral anions.

36. A cosmetic treatment process for giving to skin an artificial coloration comprising,
applying to the skin an effective amount of a composition comprising,
at least one self-tanning agent chosen from monocarbonyl compounds and polycarbonyl compounds, and
at least one flavylium salt compound which is unsubstituted in position 3, which is substituted with at least one radical chosen from hydroxyl and alkoxy radicals and which is obtained in a manner chosen from synthetically, from a plant extract containing it, and from an enriched plant extract containing it.

37. The process according to claim 36, wherein the at least one flavylium salt compound corresponds to formula (I) below:

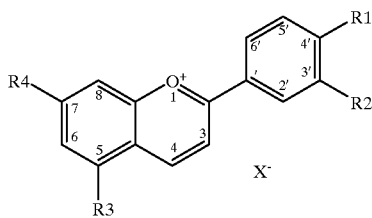

wherein:
R₁ is chosen from an OH radical and linear and branched, saturated and unsaturated ($C_1$-$C_8$) alkoxy radicals, R₂, R₃ and R₄, which may be identical or different, are chosen from H and R₁, it being understood that at least one of the radicals R₁ to R₄ is OH, X⁻ is chosen from organic anions and mineral anions.

38. A method of making a cosmetic and/or dermatological composition with the aim of giving skin an artificial coloration comprising, combining
   at least one self-tanning agent chosen from monocarbonyl compounds and polycarbonyl compounds, and
   at least one flavylium salt compound which is not substituted in position 3 and which is substituted with at least one radical chosen from hydroxyl and alkoxy radicals.

39. The method according to claim 38, wherein the artificial coloration is close to that of a natural tan.

40. The method according to claim 38, wherein the at least one flavylium salt compound corresponds to formula (I) below:

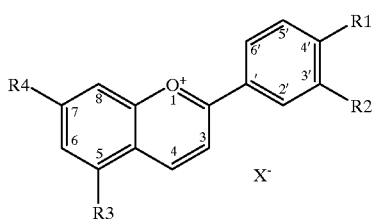

wherein:
R₁ is chosen from an OH radical and linear and branched, saturated and unsaturated ($C_1$-$C_8$) alkoxy radicals, R₂, R₃ and R₄, which may be identical or different, are chosen from H and R₁, it being understood that at least one of the radicals R₁ to R₄ is OH, X⁻ is chosen from organic anions and mineral anions.

41. A method of making a cosmetic and/or dermatological composition with the aim of giving skin an artificial coloration comprising, combining
   at least one self-tanning agent chosen from monocarbonyl compounds and polycarbonyl compounds, and
   at least one flavylium salt compound which is not substituted in position 3, which is substituted with at least one radical chosen from hydroxyl and alkoxy radicals and which is obtained in a manner chosen from synthetically, from a plant extract containing it, and from an enriched plant extract containing it.

42. The method according to claim 41, wherein the at least one flavylium salt compound corresponds to formula (I) below:

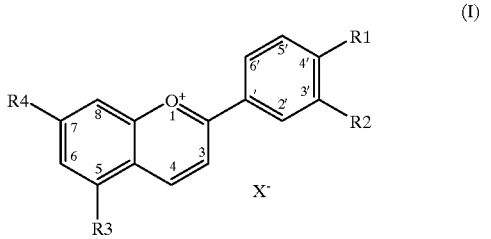

wherein:
R₁ is chosen from an OH radical and linear and branched, saturated and unsaturated ($C_1$-$C_8$) alkoxy radicals, R₂, R₃ and R₄, which may be identical or different, are chosen from H and R₁, it being understood that at least one of the radicals R₁ to R₄ is OH, X⁻ is chosen from organic anions and mineral anions.

* * * * *

UNITED STATES PATENT AND TRADEMARK OFFICE
CERTIFICATE OF CORRECTION

PATENT NO.    : 6,537,528 B2
DATED         : March 25, 2003
INVENTOR(S)   : Didier Candau et al.

It is certified that error appears in the above-identified patent and that said Letters Patent is hereby corrected as shown below:

Column 10,
Line 16, "2 mg/cm2," should read -- 2 mg/cm$^2$, --.

Column 11,
Line 29, "is is" should read -- is --.

Signed and Sealed this

Fifteenth Day of July, 2003

JAMES E. ROGAN
*Director of the United States Patent and Trademark Office*